United States Patent
Fathollahzadeh

(10) Patent No.: US 6,983,663 B2
(45) Date of Patent: Jan. 10, 2006

(54) FLOW METER ARRANGEMENT

(75) Inventor: Kiomars Fathollahzadeh, Jarfalla (SE)

(73) Assignee: Maquet Critical Care AB, Solna (SE)

( * ) Notice: Subject to any disclaimer, the term of this patent is extended or adjusted under 35 U.S.C. 154(b) by 52 days.

(21) Appl. No.: 10/777,836

(22) Filed: Feb. 12, 2004

(65) Prior Publication Data

US 2004/0167419 A1 Aug. 26, 2004

(30) Foreign Application Priority Data

Feb. 26, 2003 (SE) ............................................. 0300505

(51) Int. Cl.
*G01F 1/44* (2006.01)

(52) U.S. Cl. ................................................. 73/861.63
(58) Field of Classification Search ................... 73/118, 73/861.18, 861.19, 861.21, 861.63
See application file for complete search history.

(56) References Cited

U.S. PATENT DOCUMENTS

| 3,735,752 A | | 5/1973 | Rodder |
| 4,142,407 A | * | 3/1979 | Kuroiwa et al. ............ 73/118.2 |
| 4,404,859 A | * | 9/1983 | Ohsawa et al. ........... 73/861.18 |
| 4,449,401 A | * | 5/1984 | Kaiser et al. .............. 73/202.5 |
| 2002/0100474 A1 | | 8/2002 | Kellner et al. |

* cited by examiner

*Primary Examiner*—Max Noori
*Assistant Examiner*—Jewel V. Thompson
(74) *Attorney, Agent, or Firm*—Schiff Hardin LLP

(57) ABSTRACT

A flow meter arrangement has a venturi-type flow meter having a tubular flow channel for conveying a gas flow to be measured and in which there is provided a constriction. The arrangement further has a hot wire flow meter having a sensing element located within the flow channel and a measurement system that receives an output from the venturi-type flow meter and an output from the hot wire flow meter, and that determines a gas flow rate therefrom.

5 Claims, 3 Drawing Sheets

FLOW METER ARRANGEMENT

BACKGROUND OF THE INVENTION

1. Field of the Invention

The present invention relates to a flow meter arrangement, especially one suitable for the measurement of respiratory gas flow associated with the breathing of a patient.

2. Description of the Prior Art

In hospitals, during for example intensive care or surgical procedures, mechanical breathing aids are used to assist or control the breathing of a patient. It is important to be able to measure gas flow to and/or from the patient since this typically provides a control parameter for the mechanical breathing aid and may also be used in the derivation of parameters descriptive of the operation and metabolism of the lung. It is also important, particularly with respect to the measurement of expiratory gas flow, which the flow meter presents a relatively small resistance to the gas flow being measured.

Venturi-type or so-called "differential pressure" flow meters are well known in the art and are particularly suited to the clinical applications mentioned above. Such a meter generally has a tubular flow channel for conveying the gas flow to be measured and having a constriction, reducing the cross-sectional area of the flow channel and providing a resistance to gas flow. Also provided is a differential pressure gauge for measuring a pressure drop within the channel that is caused by the constriction. This pressure drop is proportional to the gas flow to be measured. For laminar flow the sensed pressure difference is directly proportional to the volume flow rate while for the more typical turbulent flow it is proportional to the square of the volume flow rate.

The venturi-type flow meter has a problem that its sensitivity and accuracy at low flow rates is relatively poor. This problem may arise particularly when the meter is employed in the measurement of gas flow to and from small children or neonates.

SUMMARY OF THE INVENTION

It is an object of the present invention to provide a flow meter arrangement which has a sensitivity and a dynamic range that are improved compared to known flow meter arrangements. This object is achieved in accordance with the principles of the present invention in a flow meter arrangement that includes a venturi-type flow meter having a tubular flow channel for conveying a gas flow to be measured, and a hot wire flow meter having a sensing element disposed in the flow channel of the venturi-type flow meter, and a measurement system that receives an output from the venturi-type flow meter and an output from the hot wire flow meter and which determines a gas flow rate in the channel from these outputs.

By providing a meter arrangement in which the output from a venturi-type flow meter is augmented at low flow rates by the output from a known hot-wire flow meter its sensitivity and dynamic range is enhanced over either one of the individual flow meter devices of which it is formed.

The output representing a flow rate measured by the venturi-type meter and the output representing the flow rate measured by the hot wire meter may be switchably selected as a basis for a determination of the flow rate by the arrangement. Switching preferably is done dependent on a comparison of a threshold value associated with each output in a manner to ensure that the output from the meter having the better sensitivity is always utilized.

Moreover, as a safety precaution, the output from the flow meter utilized in the determination of the flow rate by the arrangement may be compared with that output from the other meter and a warning provided by the arrangement if a difference between the two outputs, or values dependent on those outputs, exceeds a predetermined threshold.

Most usefully the sensing element of the hot wire flow meter may be disposed in the flow conduit at a location to measure flow in the region of increased flow speed caused by the constriction. This increases the sensitivity of the meter to small changes in the gas flow rate to be measured.

DESCRIPTION OF THE PREFERRED EMBODIMENTS

Figure 1:
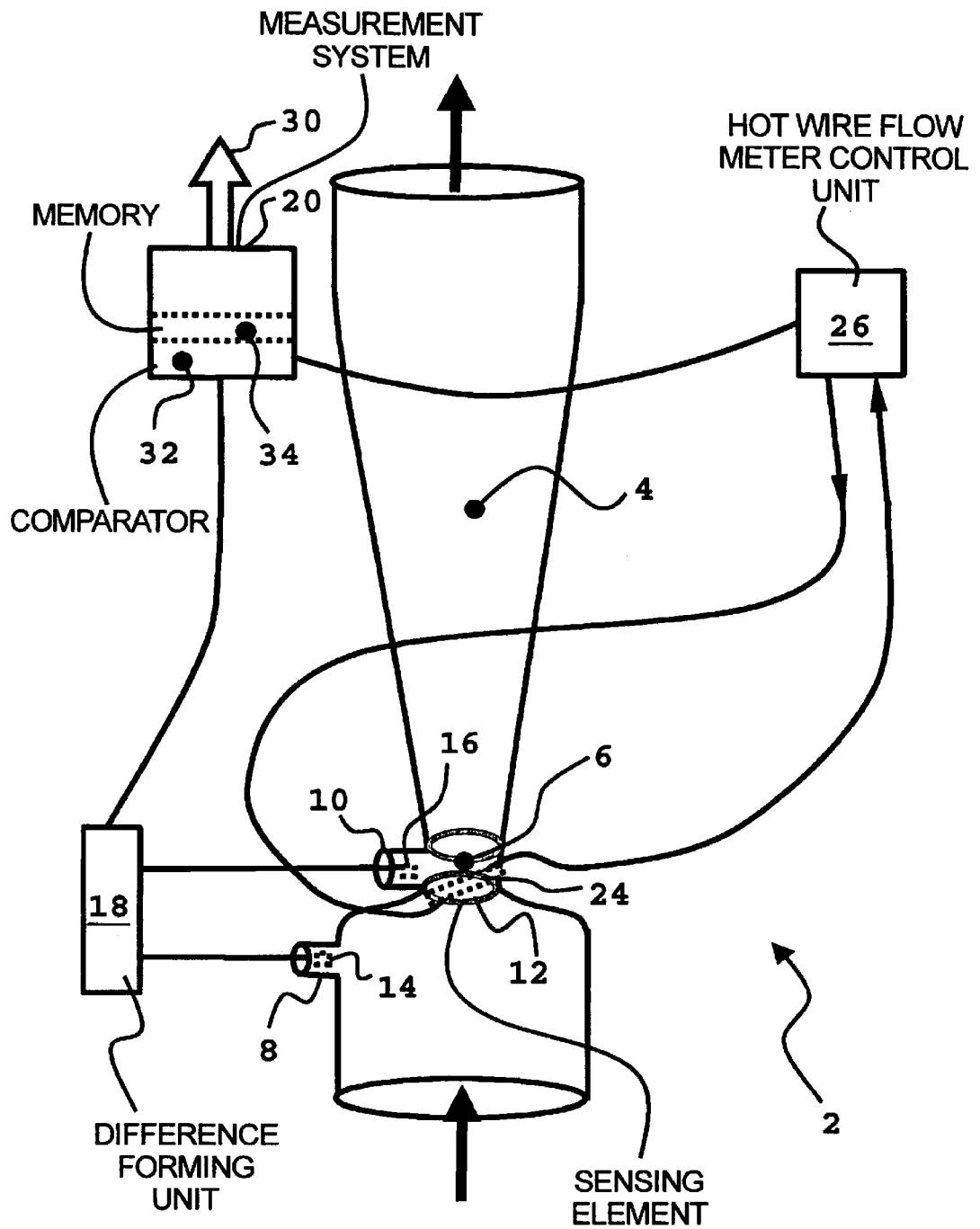
FIG. 1 is a schematic illustration of a meter arrangement according to the present invention.

In the flow meter arrangement 2 of FIG. 1 a tubular flow channel 4 has a constriction 6, formed as a neck, within it and is intended for conveying a gas flow to be measured through it in a direction indicated by the arrows. The flow channel 4 is also constructed with a first pressure port 8 and a second pressure port 10 which are disposed for pressure communication with gas in the channel 4 at locations respectively before and after an entrance 12 to the constriction 6 so as to enable a measurement to be made of a pressure drop within the channel 4 caused by gas flowing through the constriction 6. A first pressure sensor 14 and a second pressure sensor 16 are positioned within the first pressure port 8 and the second pressure port 10 respectively to supply a measure of the pressure $P_1, P_2$ respectively at those locations to a difference forming unit 18.

The difference-forming unit 18 of the present embodiment is configured in a known manner to form a pressure difference value $\Delta P$ as:

$$\Delta P = P_1 - P_2 \qquad (1)$$

which is supplied to a measurement system 20. Alternatively, a known differential pressure sensor (not shown) may be connected to the two pressure ports 8,10 that has an output indicative of the pressure difference value $\Delta P$ that may be supplied directly to the measurement system 20.

It will be appreciated by those skilled in the art that the configuration described above operates as a known venturi-type flow meter.

It is well known that the pressure difference $\Delta P$ is related to the gas flow rate within the channel 4 according to the equation:

$$\Delta P = K^*(\delta\phi/\delta t)^2 \qquad (2)$$

wherein K is a constant dependent upon, among other things, the cross-sectional areas of the flow channel 4 in the regions of the pressure ports 8,10; and $\delta\phi/\delta t$ is the volume flow rate of the gas, the flow rate of which is to be measured.

Figure 2A:
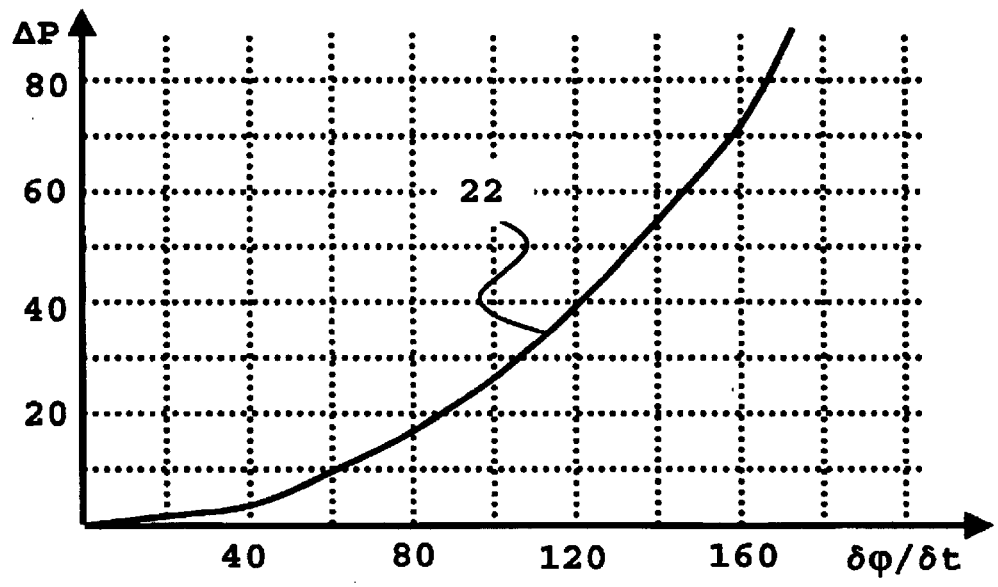
FIG. 2a is a diagrammatic representation of a pressure response characteristic of a typical venturi-type flow meter used in the arrangement of FIG. 1.
Figure 2B:
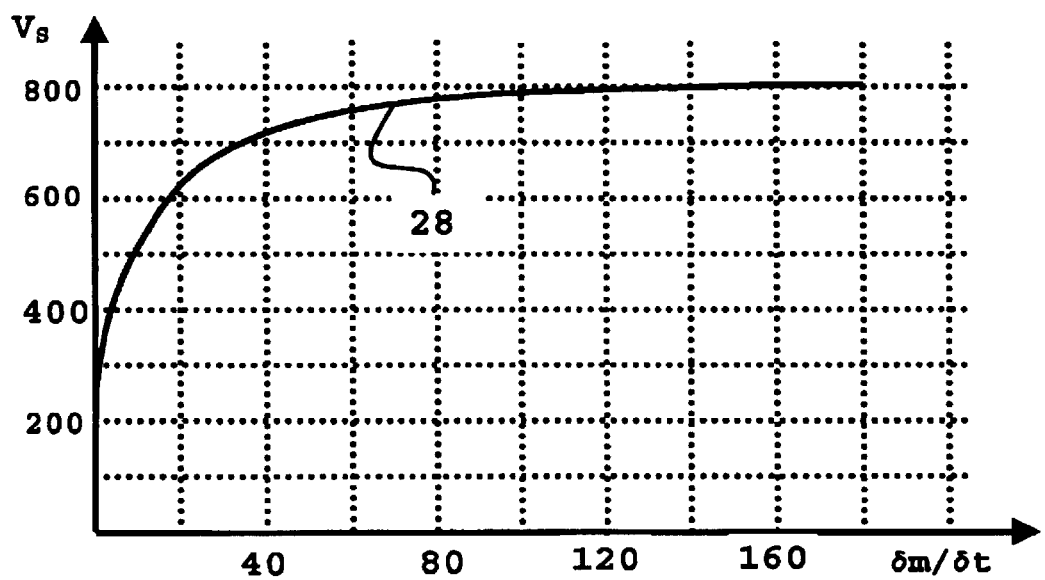
FIG. 2b is a diagrammatic representation of a voltage response characteristic of a typical hot wire flow meter used in the arrangement of FIG. 1.

A typical pressure response characteristic of this venturi-type flow meter, calculated from equation (2), is illustrated by the plot of ΔP (mbar) against δφ/δt (1 min$^{-1}$) which is shown in FIG. 2a. As can be seen from the characteristic curve 22 the venturi-type meter provides high sensitivity at higher flow rates but the resolution is much poorer at lower flow rates.

Returning to the flow meter arrangement 2 of FIG. 1, a sensing element 24 of a known hot wire flow meter is located within the flow channel 4, preferably proximal the entrance 12 to the constriction 6, that is, in the region of increased flow velocity in the channel 4. A control unit 26 of the hot wire flow meter is provided in electrical connection with the sensing element 24 and operates in a known manner to vary a current supplied to the sensing element 24 so as to maintain it at a known temperature as gas flows within the flow channel 4 and to provide an output indicative of the supplied current, for example a measure of output voltage $V_s$ of the sensing element 24, which may be expressed according to the known equation:

$$V_s = [C_0 R_s A(T_s - T_f) + C_1 R_s A(T_s - T_f)(\delta m/\delta t)^{0.5}]^{0.5} \quad (3)$$

where $R_s$ is the resistance of the sensor element 24; $T_s$ is the temperature of the element 24; $T_f$ is the temperature of the gas flow; A is the heat transfer area; $C_0$ and $C_1$ are constants depending on the properties of the gas; and δm/δt is the mass flow rate of the gas.

As can be seen from equation (3) the output signal from the control unit 26 is related to the gas flow rate by the ¼ power. A typical voltage response characteristic of this hot wire flow meter, calculated after equation (3), is illustrated by the plot of $V_s$ (mv) against δm/δt (1 min$^{-1}$) that is shown in FIG. 2a. As can be seen from the characteristic curve 28 the hot wire flow meter provides high sensitivity at lower flow rates but rapidly looses sensitivity as the flow rates increase.

Returning now to the flow meter arrangement 2 of FIG. 1, the measurement system 20 is, in the present embodiment, programmed to employ the output from either the difference forming unit 18 or the control unit 26 in making a determination of the gas flow rate in a manner described in more detail below and to provide an output 30 indicative thereof.

A comparator 32 is provided as a part of the measurement system 20 and may be realized through suitable programming of the microprocessor of the system 20. The comparator 32 is adapted to compare the outputs from the units 18,26 of the respective venturi-type flow meter and the hot wire flow meter with an associated threshold value that may be stored within a memory 34 that is included in the measurement system 20. The selection of the output from either the difference forming unit 18 or the control unit 26 as a current output by which the flow rate is to be determined is made within the measurement system 20 in dependence of the results of the comparison carried out by the comparator 32. The measurement system 20 operates to make the selection, which provides a best sensitivity for the flow meter arrangement 2 at the prevailing gas flow with the flow channel 4 based on the characteristics of the venturi and the hot wire flow meters.

Figure 3:
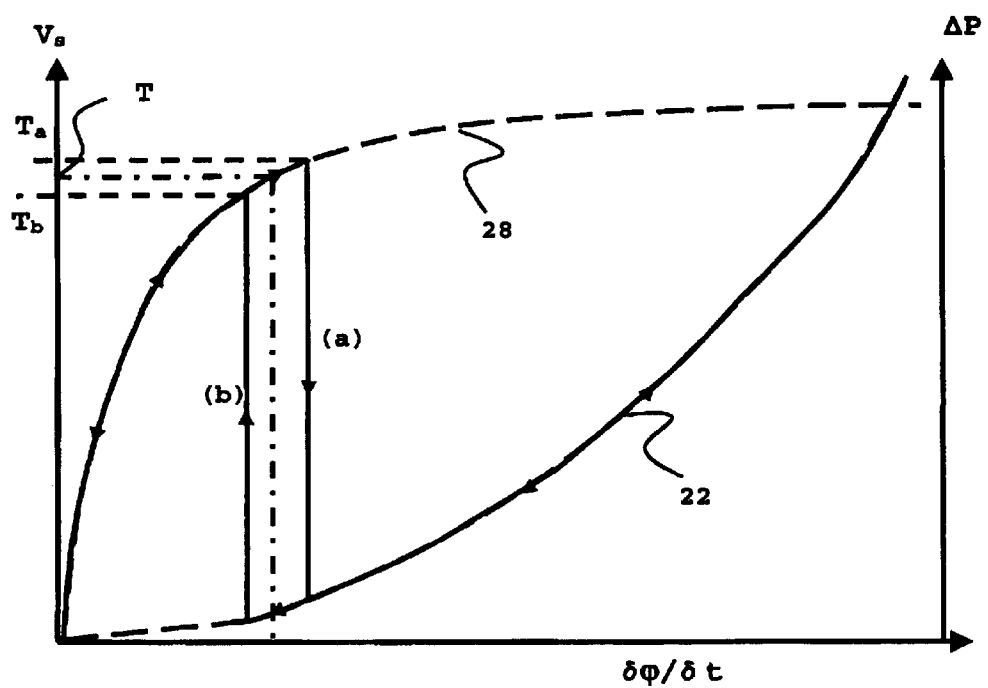
FIG. 3 is a diagrammatic representation of a measurement response characteristic of an arrangement according to FIG. 1.

In one embodiment of the arrangement 2 of FIG. 1 and with reference to its measurement response characteristic curve depicted in FIG. 3, the memory 34 stores a threshold value T which is associated with the output from the control unit 26 indicative of a flow rate of gas through the channel 4 at which the sensitivities of the venturi-type flow meter and the hot wire flow meter are substantially the same. As can be seen from the response characteristic curves 22,28 the sensitivity of the venturi-type flow meter (curve 22) decreases for flow rates lower than this threshold T whilst the sensitivity of the hot wire flow meter (curve 28) decreases for flow rates higher than this threshold T. The comparator 32 of the measurement system 20 is programmed to compare the threshold value T with the output from one or both of the difference forming unit 18 and the control unit 26 (in the present example only the output from the control unit 26 is utilized). From this comparison the measurement system 20 is programmed to employ the output from the difference forming unit 18 in the determination of the flow rate of gas within the channel 4 if the output from the control unit 26 is greater than the threshold value T and to employ the output from the control unit 26 in the determination of the flow rate of gas within the channel 4 if the output from the control unit 26 is less than the threshold value T.

According to a further embodiment of the arrangement 2 of FIG. 1 the measurement system 20 may be adapted so that the comparator 32 employs two different threshold values $T_a$ and $T_b$, on each side of the original threshold value T. Instability in the arrangement 2 when the gas flow to be measured is of the order of the flow value for which the threshold T is set may thus be avoided. This is also illustrated in FIG. 3. As shown, the output from the control unit 26 of the hot wire sensor is used in the range from zero to the threshold $T_a$. From this point (curve (a)) and upwards the output from the difference forming unit 18 of the venturi-type flow meter is used. When the currently selected output is from the difference forming unit 18 then the threshold value $T_b$ is employed in the comparator 32 in order to determine when the currently selected output should be switched to that from the difference forming unit 18. From this point (curve (b)) and downwards the output from the control unit 26 of the hot wire flow meter is used.

The memory 34 stores the threshold values T, $T_a$ or $T_b$ that are required to be accessed by the comparator 32. Look-up tables that index values of output signals from each of the difference forming unit 18 and the control unit 26 with actual flow rates also may be stored within the memory 34. The measurement system 20 may then be adapted to access the appropriate table within the memory 34 dependent on the result of the comparison within the comparator 32 in order to provide the output 30 that indicates the value of the flow rate being measured within the tubular flow channel 4. These look-up tables may be constructed by calibrating the outputs of the units 18,26 of each meter with known gas flow rates through the channel 4 and the results input into the memory 34. This may of course be done for each arrangement individually or batch-wise, employing a common look-up table for theoretically identical meters.

As a safety precaution the measurement system 20 may be further modified to compare, for example within the comparator 32, values, such as flow values obtained using the look-up tables, dependent on the outputs from both units 18,26 and to provide, as a component of the output signal 30, a warning in the event that the difference between the values exceeds a pre-determined threshold ($T_s$), which may also be held in the memory 34.

It will be appreciated that while the difference forming unit 18, the control unit 26 and the measurement system 20 are disclosed with regard to the arrangement 2 of FIG. 1 as being physically separate units some or all of the functionality of a plurality of these different units may be provided in a single device, such as a microprocessor suitably programmed using known programming techniques, without departing from the invention.

Moreover, it will be appreciated that the output signals from the venturi-type flow meter and the hot wire flow meter may be utilized in a number of different ways, such as by addition and normalization of the two signals, in order to achieve a flow meter arrangement having a sensitivity across its measurement range that is enhanced over the sensitivity of either one of the constituent meters, without departing from the invention as claimed. Suitable empirically derived look-up tables or formulae may be constructed without undue effort in order to index the results of a particular utilisation with the actual flow rate of gas within the channel 4.

Although modifications and changes may be suggested by those skilled in the art, it is the intention of the inventor to embody within the patent warranted hereon all changes and modifications as reasonably and properly come within the scope of the inventor's contribution to the art.

I claim:

1. A flow meter arrangement comprising:

a venturi-type flow meter having a tubular flow channel for conveying a gas flow to be measured, said venturi-type flow meter emitting an output;

a hot wire flow meter having a sensing element disposed in said flow channel of said venturi-type flow meter, said hot wire flow meter generating an output separate from said output of said venture-type flow meter; and a measurement system connected to said venturi-type flow meter and to said hot wire flow meter to receive the respective outputs therefrom, said measurement system determining a gas flow rate in said flow channel from said outputs.

2. A flow meter arrangement as claimed in claim 1 wherein said measurement system comprises a comparator for comparing at least one of said outputs to a threshold value to obtain a comparison result and which, dependent on said comparison result switchably selects one of said venturi-type flow meter and said hot wire flow meter to provide an output, as a currently selected output, and wherein said measurement system determines said gas flow rate only from said currently selected output.

3. A flow meter arrangement as claimed in claim 2 wherein each of said venturi-type flow meter and said hot wire flow meter has a sensitivity, and wherein said comparator compares said output from at least one of said venturi-type flow meter and said hot wire flow meter to a threshold value representing a sensitivity at which the respective sensitivities of said venturi-type flow meter and said hot wire flow meter are substantially equal.

4. A flow meter arrangement as claimed in claim 2 wherein said threshold value is a first threshold value, and wherein said measurement system comprises a memory containing a second threshold value associated with the output of the venturi-type flow meter and a third threshold value associated with the output of the hot wire flow meter, said second and third threshold values being respectively indicative of different gas flow rates, and wherein said comparator has access to said memory and compares said currently selected output with the respective second or third threshold from said memory associated with said currently selected output.

5. A flow meter arrangement as claimed in claim 1 wherein said measurement system comprises a difference former for forming a difference value between the output from the venturi-type flow meter and the output from the hot wire flow meter, and a comparator for determining if said difference value exceeds a predetermined threshold.

* * * * *